(12) United States Patent
Ikekawa et al.

(10) Patent No.: US 6,783,771 B2
(45) Date of Patent: Aug. 31, 2004

(54) PHYSIOLOGICALLY ACTIVE SUBSTANCE EEM-S ORIGINATING IN MUSHROOMS, PROCESS FOR PRODUCING THE SAME AND DRUGS

(75) Inventors: Tetsuro Ikekawa, Chiba (JP); Akiko Ikekawa, Chiba (JP); Fumitake Shimada, Tokyo (JP)

(73) Assignee: Life Science Laboratories Co., Ltd., Chiba (JP)

( * ) Notice: Subject to any disclaimer, the term of this patent is extended or adjusted under 35 U.S.C. 154(b) by 0 days.

(21) Appl. No.: 10/169,099

(22) PCT Filed: Jan. 11, 2001

(86) PCT No.: PCT/JP01/00072

§ 371 (c)(1),
(2), (4) Date: Jul. 12, 2002

(87) PCT Pub. No.: WO01/51010

PCT Pub. Date: Jul. 19, 2001

(65) Prior Publication Data

US 2003/0012798 A1 Jan. 16, 2003

(30) Foreign Application Priority Data

Jan. 12, 2000 (JP) ........................................ 2000-037220

(51) Int. Cl.[7] .......................... A61K 35/84; A61K 9/62; A61K 9/28; A61K 9/16
(52) U.S. Cl. .................. 424/461; 424/195.15; 424/474; 424/477; 424/490; 424/491
(58) Field of Search ............................. 424/195.15, 461, 424/474, 477, 490, 491

(56) References Cited

U.S. PATENT DOCUMENTS

| | | | | |
|---|---|---|---|---|
| 4,461,760 A | * | 7/1984 | Sugano et al. | 514/2 |
| 5,302,699 A | * | 4/1994 | Kawamura et al. | 530/371 |
| 5,334,704 A | * | 8/1994 | Tsunoo et al. | 530/371 |
| 5,711,948 A | * | 1/1998 | Pospelova et al. | 424/773 |
| 5,714,464 A | * | 2/1998 | Piraino et al. | 514/12 |
| 6,440,420 B1 | * | 8/2002 | Liu et al. | 424/195.15 |

FOREIGN PATENT DOCUMENTS

| | | |
|---|---|---|
| JP | 56-057716 | 5/1981 |
| JP | 56-127317 | 10/1981 |
| JP | 62-19530 | 1/1987 |
| JP | 63-72629 | 4/1988 |
| JP | 08-291078 | 11/1996 |
| JP | 09-315994 | 12/1997 |
| JP | 2000-159808 | 6/2000 |
| WO | WO 99/53937 | 10/1999 |

OTHER PUBLICATIONS

Derwent Abstracts, AN 1985–066430, XP–002236709, JP 60–023392, Feb. 5, 1985.
Patent Abstracts of Japan, JP 57–206618, Dec. 18, 1982.
Derwent Abstracts, AN 1985–066429, XP–002236710, JP 60–023391, Feb. 5, 1985.
Patent Abstracts of Japan, JP 63–072629, Apr. 2, 1988.
Patent Abstracts of Japan, JP 62–019530, Jan. 28, 1987.
Patent Abstracts of Japan, JP 56–127317, Oct. 6, 1981.
T. Ikekawa, et al., Chem. Pharm. Bull, vol. 40, No. 7, pp. 1954–1957, XP–001146586, "Antitumor Activity of Hypsizigus Marmoreus. I. Antitumor Activity of Extracts and Polysaccharides", 1995.
H. Saitoh, et al., Pharmaceutical Society of Japan, vol. 117, No. 12, pp. 1006–1010, XP–009008577, "Antitumor Activity of Hypsizigus Marmoreus. II. Preventive Effect Against Lung Metastasis of Lewis Lung Carcinoma", 1997.
K. Tsuchida, et al., The Journal of Biological Chemistry, vol. 270, No. 4, pp. 1481–1484, XP–001146585, "Isolation of a Novel Collagen–Binding Protein from the Mushroom, Hypsizigus Marmoreus, Which Inhibits The Lewis Lung Carcinoma Cell Adhesion to Type IV Collagen", 1995.
T. Matsuzawa, et al., Yakugaku Zasshi, vol. 118, No. 10, pp. 476–481, XP–009008578, "Studies on Antioxidant Effects of Hypsizigus Marmoreus. II." Effects of Hypsizigus Marmoreus For Antioxidant Activities of Tumor–Bearing Mice, Oct. 1998.

* cited by examiner

Primary Examiner—Herbert J. Lilling
(74) Attorney, Agent, or Firm—Oblon, Spivak, McClelland, Maier & Neustadt, P.C.

(57) ABSTRACT

EEM-S obtained by extracting with hot water or a lower alcohol at least one mushroom selected from among *Lentinus edodes, Flammulina velutipes, Hypsizigus marmoreus, Pleurotus ostreatus, Pholiota nameko, Grifola fondosa, Volvariella speciosa* ver. *speciosa, Lyophllum decastes*, blanc du pays, *Tricholoma matsutake, Ganoderma lucidum* and *Phellinus yucatensis*, treating the obtained extract by the molecular sieve method and thus eliminating low-molecular-weight and high-molecular-weight fractions: and preparations thereof. This EEM-S exerts physiological effects such as anticancer, immunopotentiating, antioxidative, hypotensive and hypoglycemic effects.

20 Claims, 6 Drawing Sheets

PHYSIOLOGICALLY ACTIVE SUBSTANCE EEM-S ORIGINATING IN MUSHROOMS, PROCESS FOR PRODUCING THE SAME AND DRUGS

TECHNICAL FIELD

The present invention relates to a substance having biological activity, such as anticancer activity, antiallergic activity, immunopotentiating activity, and antioxidation activity, obtained from at least one edible mushroom selected from *Lentinus edodes, Flammulina velutipes, Hypsizygus marmoreus, Pleurotus ostreatus, Grifola fondosa, Volvariella speciosa* ver. *speciosa, Pholiota nameko, Lyophllum decastes*, Blanc du pays, *Tricholoma matsutake*, and Bracket fungi such as *Ganoderma lucidum* and *Phellinus yucatensis* (*Phellinus linteus*), a process for producing the substance, and a preparation containing the biologically active substance.

BACKGROUND ART

The present inventors have conducted extensive studies on biological activity of mushrooms for many years. It is known in the art that some species of mushrooms exhibit biological activity such as anticancer effects, immunopotentiating effects, antioxidative effects, hypotensive and hypoglycemic effects. However, mushrooms having no or only a small degree of activity are also advertised as being very efficacious and put on the market.

The present inventors have found that the anticancer effects of mushrooms originate from polysaccarides contained therein from the research results based on a mass of research data, and have conducted studies on a glucan which is the polysaccaride contained in mushrooms. However, the present inventors have found that the glucan, which is a pure simple polysaccaride, exhibits activity by injection, but does not exhibit effects by oral administration.

Since the administration by injection can be carried out only in the hospital or the like and oral administration causes a person less pain, provision of active components from mushrooms effective through oral administration has been strongly demanded.

Accordingly, an object of the present invention is to provide a method for efficiently extracting a biologically active substance exhibiting biological activity such as anticancer activity and immunopotentiating activity through oral administration from mushrooms containing a high concentration of such a substance, and a preparation containing the biologically active substance suitably prepared for use.

DISCLOSURE OF THE INVENTION

As a result of extensive studies to achieve the above object, the present inventors have found that fruit bodies and/or mycelia of edible mushrooms contain a large amount of active substances effective through oral administration. The active substances effective through oral administration are contained in an extract of the mushrooms with water, a hydrophilic solvent, or a mixed solvent of these. The present inventors have found that a fraction having a specific molecular weight range obtained by removing low-molecular-weight and high-molecular-weight fractions from the extract using a molecular sieve method exhibits excellent biological activity. This finding has led to the completion of the present invention.

Specifically, the present invention provides a biologically active substance EEM-S obtained by extracting at least one mushroom selected from *Lentinus edodes, Flammulina velutipes, Hypsizygus marmoreus, Pleurotus ostreatus, Pholiota nameko, Grifola fondosa, Volvariella speciosa* ver. *speciosa, Lyophllum decastes*, Blanc du pays, *Tricholoma matsutake, Ganoderma lucidum*, and *Phellinus yucatensis* (*Phellinus linteus*), with water, a hydrophilic solvent, or a mixed solvent of these, and collecting a fraction having a molecular weight of 6,000–60,000 from the extract using a molecular sieve method.

The present invention also provides a process for producing the biologically active substance EEM-S.

BEST MODE FOR CARRYING OUT THE INVENTION

Figure 1:
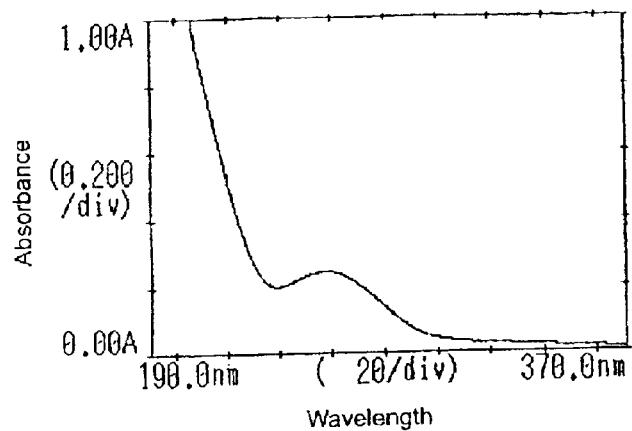
FIG. 1 is a view showing an ultraviolet and visible absorption curve of a biologically active substance EEM-SB obtained in Example 1, in which the solvent is water.

The biologically active substance EEM-S of the present invention is obtained by extracting, with water and/or a hydrophilic solvent, a finely ground product of fruit bodies and/or mycelia of at least one edible mushroom such as *Lentinus edodes, Flammulina velutipes, Hypsizygus marmoreus, Pleurotus ostreatus, Pholiota nameko, Grifola fondosa, Volvariella speciosa* ver. *speciosa, Lyophllum decastes*, Blanc du pays, *Tricholoma matsutake, Ganoderma lucidum*, or *Phellinus yucatensis* (*Phellinus linteus*) (hereinafter referred to as "mushroom"). As the hydrophilic solvent used for extraction, a lower alcohol having 1–4 carbon atoms is preferably used.

A fraction containing the biologically active substance EEM-S is extracted from the mushroom by adding an appropriate amount of water or a hydrophilic solvent such as a lower alcohol to the raw material mushroom, and extracting the fraction under reflux at a temperature of 80–98° C., and preferably 90–98° C. in the case of using water, for about 1–4 hours, and preferably 2–4 hours, for example. The amount of solvent used for extraction is about three to ten times the weight of the mushroom.

After optionally separating solid impurities from the resulting extract by filtration or the like, the solvent is evaporated under reduced pressure to obtain a solid extract.

The solid extract thus obtained exhibits activity through oral administration and may be used as is. However, the activity can be increased by using a fraction having a molecular weight of 6,000–60,000 obtained by removing an unnecessary portion from the extract using a molecular sieve and concentrating the resulting product under reduced pressure as the biologically active substance EEM-S.

As the molecular sieve used for the above purpose, a molecular sieve membrane (flat membrane), hollow filter membrane, permeable membrane, molecular sieve chromatography, and the like can be given. The biologically active substance EEM-S may be separated by appropriately applying a method using these molecular sieves.

A method of separating the biologically active substance EEM-S is described below taking a case of using a module-type hollow filter membrane as an example. The extract of the mushroom with water and/or a hydrophilic solvent (fraction containing the biologically active substance EEM-S) is treated using a low-molecular-weight fraction membrane module such as AIP-3013, AIP-2013, or AIP-1010 (manufactured by Asahi Kasei Corporation) to remove low-molecular-weight substances (substances having a molecular weight of 6,000 or less). The concentrate from which the low-molecular-weight substances are removed is treated using a high-molecular-weight fraction membrane module such as AHP-3013, AHP-2013, or AHP-1010 (manufactured by Asahi Kasei Corporation) to remove high-molecular-weight substances (substances having a molecular weight of 60,000 or more). The resulting solution is concentrated using a low-molecular-weight fraction membrane module. A biologically active substance EEM-S having a molecular weight of 6,000–60,000 is obtained in this manner.

In the case of using the molecular sieve method, the molecular weight may differ from the molecular weight determined using other methods, since the substances are sifted differently depending upon the shape of the molecules. In the present invention, the molecular weight refers to a molecular weight determined using the molecular sieve method. More precisely, the molecular weight on the low-molecular-weight side is a value measured using AIP-3013 or a low-molecular-weight fraction membrane module equal to AIP-3013. Similarly, the molecular weight on the high-molecular-weight side is a value measured using AHP-3013 or a high-molecular-weight fraction membrane module equal to AHP-3013.

The biologically active substances of the mushrooms thus obtained are collectively referred to as EEM-S. However, in the case of using the mycelia of the mushrooms as the raw material, the yield of the biologically active substance varies depending upon culture conditions. Therefore, it is necessary to select an optimum culture medium, culture temperature, and the like. Moreover, physicochemical properties may differ depending upon the species of mushrooms.

For example, the biologically active substance EEM-S produced using *Hypsizygus marmoreus* as the raw material (hereinafter may be called "EEM-SB") exhibits physicochemical properties shown in Example 1. The biologically active substance EEM-S produced using *Flammulina velutipes* as the raw material (hereinafter may be called "EEM-SE") exhibits physicochemical properties shown in Example 5. The biologically active substances EEM-S produced using *Lentinus edodes, Grifola fondosa*, and *Pholiota nameko*, respectively, as the raw material (hereinafter may be called "EEM-SS", "EEM-SM", and "EEM-SN", respectively) have ultraviolet and visible absorption shown in FIGS. 1 to 5.

Although there are small differences in the physicochemical properties, these biologically active substances exhibit high biological activity in comparison with a simple hot water extract of each mushroom, as shown in Example 6. Therefore, these biologically active substances are considered to have common properties.

The above-described biologically active substance EEM-S exhibits biological activity through oral administration. The dose of EEM-S through oral administration to obtain the predetermined effects differs depending upon the age and the weight of a person, purpose, and the like. The dose of EEM-S is generally 200–5000 mg, and preferably 1000–3000 mg per day for an adult. It is suitable that the above amount be separately administered several times per day.

The biologically active substance EEM-S of the present invention may be prepared as a powdered preparation, granule preparation, capsule preparation, or liquid preparation using a conventional method. However, since the biologically active substance EEM-S may be discolored or deteriorate when allowed to stand in air due to absorption of moisture, it is preferable to use the biologically active substance EEM-S as a tablet provided with a film coat. As the film coat material, a soybean peptide, a shell resin material, and the like are preferable. Absorption of moisture may not be securely prevented using other film coat materials, whereby the biologically active substance may be discolored or deteriorate.

EXAMPLES

The present invention is described below in more detail by examples. The following examples take anticancer effects as an example of the biological activity. However, the biological activity of the substance of the present invention is not limited to the anticancer effects. The substance of the present invention has the above-described biological activity.

Example 1

1000 g of *Hypsizygus marmoreus* was finely ground and extracted with hot water. A precipitate was removed from the resulting extract using a PS-88 membrane (manufactured by Ohtsuka Jitsugyo Co., Ltd.). A fraction containing high-molecular-weight substances (molecular weight of 6, 000 or more) was concentrated from the hot water extract using a module-type hollow filter membrane for low-molecular-weight fractions ("AIP-3013" manufactured by Asahi Kasei Corporation) High-molecular-weight substances (molecular weight of 50,000 or more) were removed from the concentrate using a module-type hollow filter membrane for high-molecular-weight fractions ("AHP-3013" manufactured by Asahi Kasei Corporation). The resulting solution was concentrated using a low-molecular-weight fraction membrane module AIP-3013. A biologically active substance EEM-SB having a molecular weight of 6,000–50,000 was obtained by the above continuous treatment.

<Physicochemical Properties of EEM-SB>

(1) Ultraviolet absorption (UV absorption at 370–190 nm in water was measured): maximum value: 258.0 nm (absorption curve is shown in FIG. 1)

Figure 6:
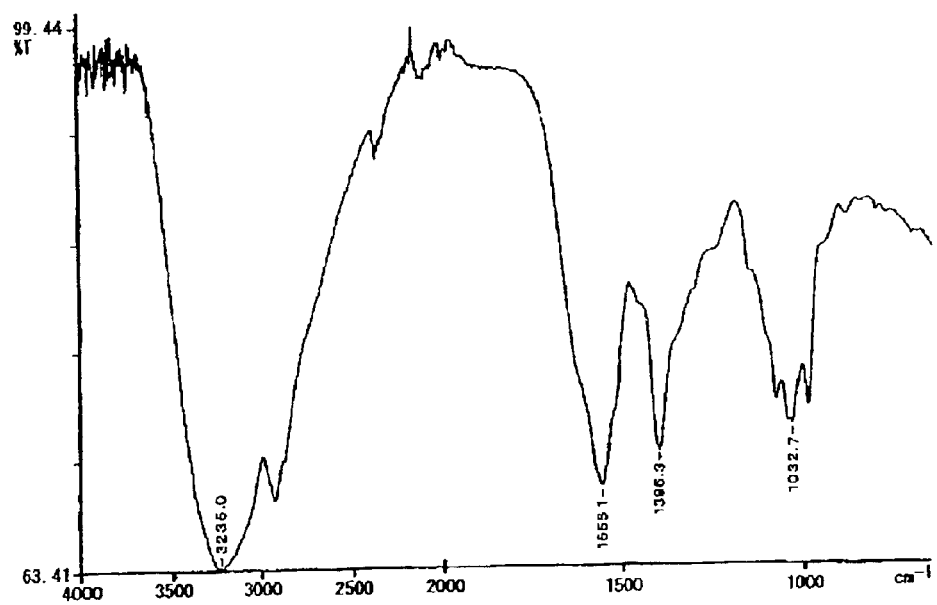
FIG. 6 is a view showing an infrared absorption curve of the biologically active substance EEM-SB obtained in Example 1 measured using an ATR method.
Figure 8:
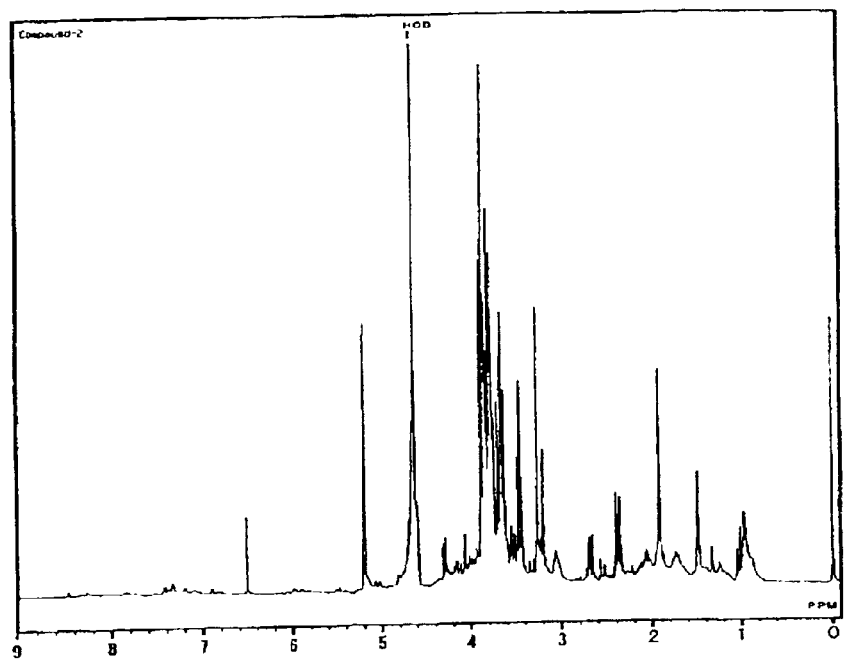
FIG. 8 is a chart showing $^1$H-NMR ($D_2O$) of the biologically active substance EEM-SB obtained in Example 1.
Figure 10:
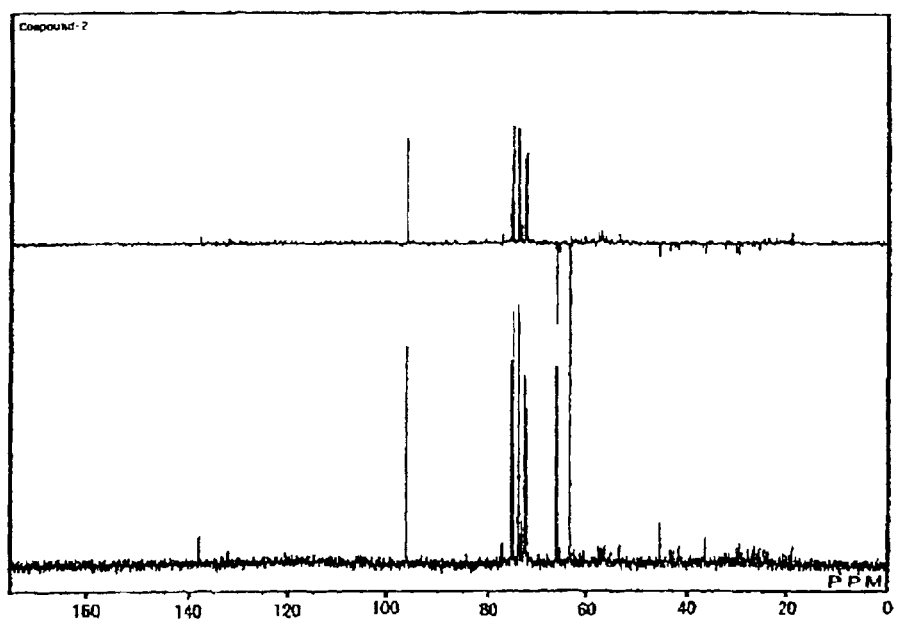
FIG. 10 is a chart showing $^{13}$C-NMR ($D_2O$) of the biologically active substance EEM-SB obtained in Example 1.

(2) Infrared absorption (measured using ATR method): maximum value (cm$^{-1}$): 218, 1560, 1396, 1032 (absorption curve is shown in FIG. 6)
(3) $^1$H-NMR (measured in D$_2$O): FIG. 8 shows the chart.
(4) $^1$C-NMR (measured in D$_2$O): FIG. 10 shows the chart.
(5) Protein content: 24.3%
(6) Carbohydrate content: 27.0%
(7) Ratio of essential carbohydrates:
glucose:galactose:mannose=18:2:1
(8) Amino acid composition: aspartic acid; 9.0%, glutamic acid; 16.1%, glycine; 9.1%, alanine; 12.5%, valine; 5.7%, arginine; 5.6%, ornithine; 7.8%
(9) Elementary analysis value: C: 36.2%, H: 6.0%, N: 5.8%

The EEM-SB thus obtained can be powdered by freeze-drying. A tablet which can be orally administered is formed by tableting the powder.

Example 2

Figure 2:
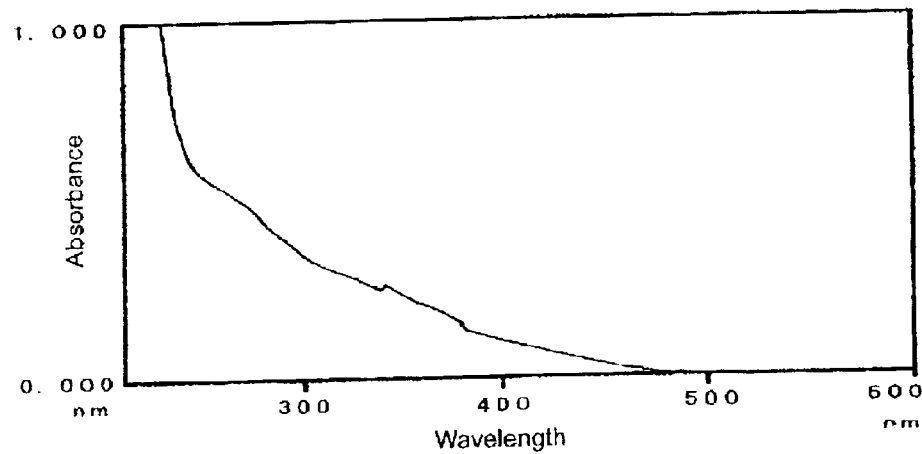
FIG. 2 is a view showing an ultraviolet and visible absorption curve of a biologically active substance EEM-SS obtained in Example 2, in which the solvent is water.

500 g of *Lentinus edodes* was ground and extracted with hot water. A precipitate was removed from the resulting extract using a PB-88 membrane (manufactured by Ohtsuka Jitsugyo Co., Ltd.). A fraction containing high-molecular-weight substances was concentrated from the hot water extract using a module-type hollow filter membrane for low-molecular-weight fractions ("AIP-3013" manufactured by Asahi Kasei Corporation) High-molecular-weight substances were removed from the concentrate using a module-type hollow filter membrane for high-molecular-weight fractions ("AHP-3013" manufactured by Asahi Kasei Corporation). The resulting solution was concentrated using a low-molecular-weight fraction membrane module AIP-3013. The ultraviolet absorption curve of the resulting biologically active substance EEM-SS in water is shown in FIG. 2.

The EEM-SS thus obtained can be powdered by freeze-drying. A tablet can be formed by tableting the powder.

Example 3

1000 g of *Grifola fondosa* was extracted with hot water. The extract was filtered by means of suction using a molecular sieve membrane ("PM-2" manufactured by Ohtsuka Jitsugyo Co., Ltd.) to remove fungus bodies. A low-molecular-weight fraction (molecular weight of 6,000 or less) was removed by dialysis with running water using a permeable membrane. A high-molecular-weight fraction was removed from the resulting solution using a hollow molecular sieve membrane (AHP-3013) to obtain a biologically active substance EEM-SM.

Figure 3:
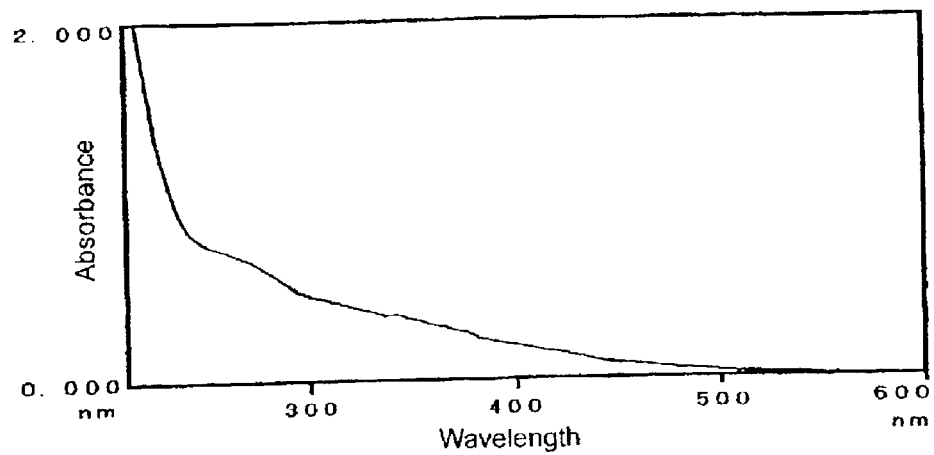
FIG. 3 is a view showing an ultraviolet and visible absorption curve of a biologically active substance EEM-SM obtained in Example 3, in which the solvent is water.

The ultraviolet absorption curve of the resulting biologically active substance EEM-SM in water is shown in FIG. 3.

Example 4

1000 g of *Pholiota nameko* was extracted with hot water. The extract was filtered by means of suction using a molecular sieve membrane ("PM-2" manufactured by Ohtsuka Jitsugyo Co., Ltd.) to remove fungus bodies. A low-molecular-weight fraction (molecular weight of 6,000 or less) was removed by dialysis with running water using a permeable membrane. A high-molecular-weight fraction was removed from the resulting solution using a hollow molecular sieve membrane (AHP-3013) to obtain a biologically active substance EEM-SN.

Figure 4:
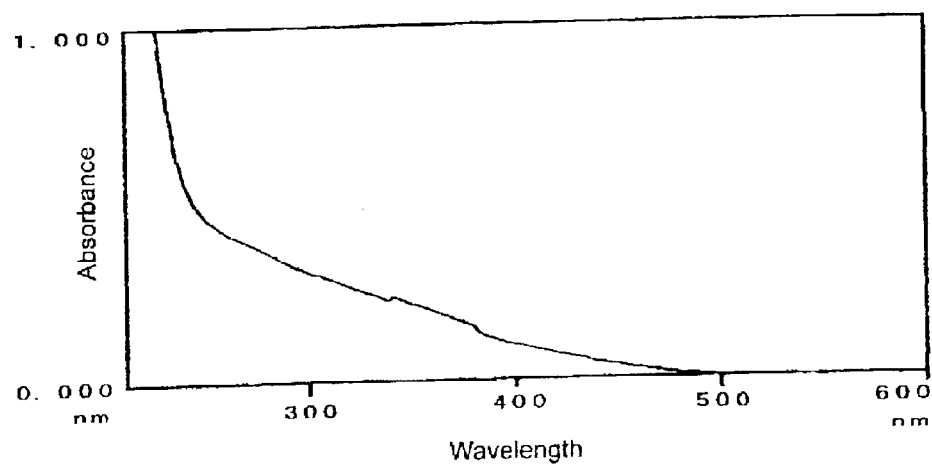
FIG. 4 is a view showing an ultraviolet and visible absorption curve of a biologically active substance EEM-SN obtained in Example 4, in which the solvent is water.

The ultraviolet absorption curve of the resulting biologically active substance EEM-SN in water is shown in FIG. 4.

Example 5

1000 g of *Flammulina velutipes* was extracted with hot water under reflux to obtain 107 g of an extract. The extract was dissolved in water and dialyzed in a dialysis tube to obtain a fraction containing high-molecular-weight substances (molecular weight of 6,000 or more) in the permeable membrane. The fraction containing high-molecular-weight substances was treated using a molecular sieve membrane PM-10 to remove high-molecular-weight substances (molecular weight of 50,000 or more), and then freeze-dried to obtain a substance containing a high concentration of EEM-SE with a molecular weight of 6,000–50,000. This substance was prepared as a powdered preparation.

<Physicochemical Properties of EEM-SE>

Figure 5:
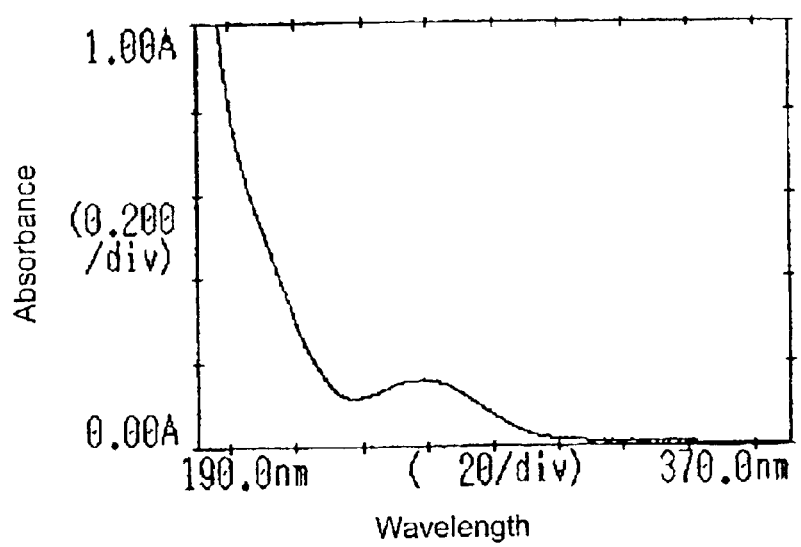
FIG. 5 is a view showing an ultraviolet and visible absorption curve of a biologically active substance EEM-SE obtained in Example 5, in which the solvent is water.
Figure 7:
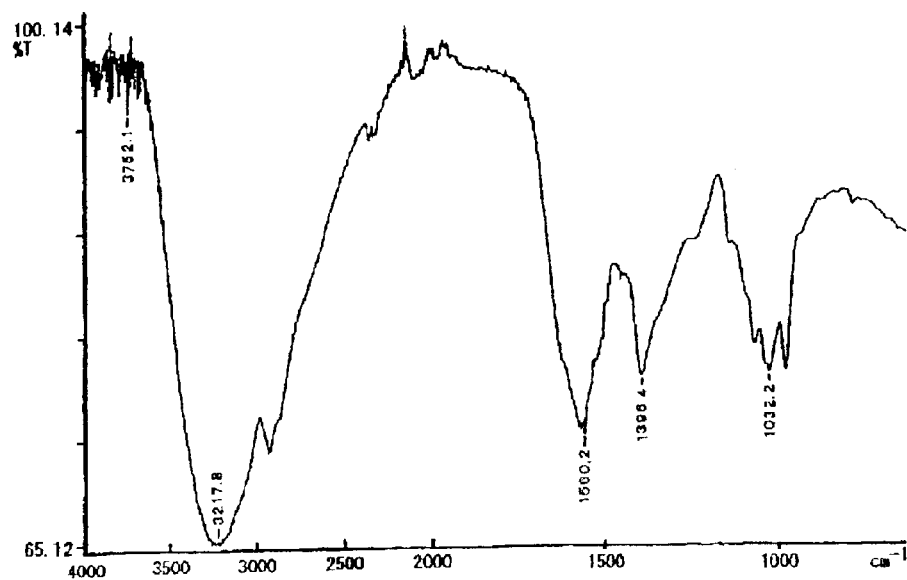
FIG. 7 is a view showing an infrared absorption curve of the biologically active substance EEM-SE obtained in Example 5 measured using an ATR method.
Figure 9:
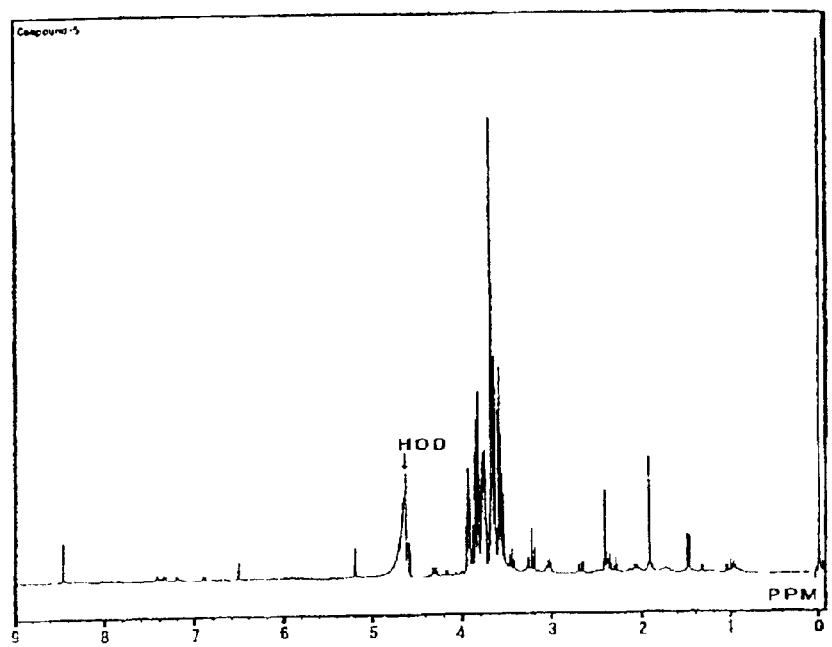
FIG. 9 is a chart showing $^1$H-NMR ($D_2O$) of the biologically active substance EEM-SE obtained in Example 5.
Figure 11:
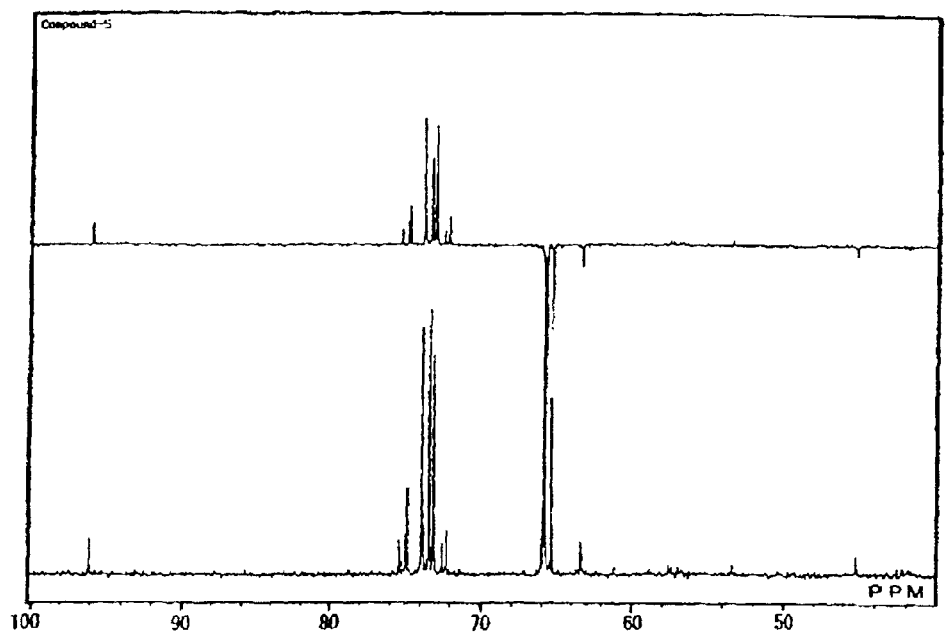
FIG. 11 is a chart showing $^{13}$C-NMR ($D_2O$) of the biologically active substance EEM-SE obtained in Example 5.

Physicochemical properties of biologically active substance EEM-SE:

(1) Ultraviolet absorption (UV absorption at 370–190 nm in water was measured): maximum value: 258.4 nm (absorption curve is shown in FIG. 5)
(2) Infrared absorption (measured using an ATR method): maximum value (cm$^{-1}$): 3279, 2927, 1578, 1400, 1043 (absorption curve is shown in FIG. 7)
(3) $^1$H-NMR (measured in D$_2$O): FIG. 9 shows the chart.
(4) $^1$C-NMR (measured in D$_2$O): FIG. 11 shows the chart.
(5) Protein content: 12.7%
(6) Carbohydrate content: 9.8%
(7) Ratio of essential carbohydrates:
glucose:galactose:mannose=16:3:1
(8) Amino acid composition: aspartic acids; 9.1%, glutamic acid; 17.7%, glycine; 14.8%, alanine; 21.9%, valine; 11.8%, arginine; 6.8%, ornithine; 12.6%
(9) Elementary analysis value: C: 36.5%, H: 6.6%, N: 3.5%

Example 6

A powdered preparation was prepared using the biologically active substance EEM-S obtained in Example 1, 2, 3, or 5, and subjected to the following anticancer test. Anticancer activity was determined by comparing the survival rate between the biologically active substances of the examples and a control group The results are shown in Table 1.

(Anticancer Test)

Female BDF1 mice were subcutaneously transplanted with viable Lewis lung carcinoma cells. The biologically active substance EEM-S obtained in each example was suspended in purified water and orally administered to the mice at a dose of 500 mg/kg per day for 20 days from the next day. The survival rate was calculated from an average survival period of the mice in a control group in which only purified water was administered, in groups in which a hot water extract of the mushroom was administered, and in groups in which the biologically active substance obtained in Examples 1, 2, 3, or 5 was administered. The results are shown in Table 1.

(Results)

TABLE 1

| Sample | Average survival period (day) | Survival rate (%) |
| --- | --- | --- |
| Control group | 26.2 | |
| *Hypsizygus marmoreus* hot water extract | 30.2 | 15.3 |
| *Lentinus edodes* hot water extract | 30.0 | 14.5 |
| *Grifola fondosa* hot water extract | 29.8 | 13.9 |
| *Flammulina velutipes* hot water extract | 30.2 | 15.1 |
| Biologically active substance EEM-SB of Example 1 | 38.2 | 45.8 |

TABLE 1-continued

| Sample | Average survival period (day) | Survival rate (%) |
|---|---|---|
| Biologically active substance EEM-SS of Example 2 | 36.0 | 37.4 |
| Biologically active substance EEM-SM of Example 3 | 35.2 | 34.4 |
| Biologically active substance EEM-SE of Example 5 | 36.8 | 40.6 |

INDUSTRIAL APPLICABILITY

According to the present invention, substances having high biological activity are easily and efficiently obtained from edible mushrooms, and products useful as drugs or health foods are obtained.

What is claimed is:

1. A biologically active substance EEM-SB obtained by extracting *Hypsizygus marmoreus* with water, a lower alcohol having 1–4 carbon atoms, or a mixed solvent of these, and treating the extract using a molecular sieve method, the biologically active substance EEM-SB having a molecular weight of 6,000–60,000, a maximum value of ultraviolet absorption in water of 255–260 nm, a maximum infrared absorption wave number of 1560, 1396, and 1032 $cm^{-1}$ (including an error of ±50 $cm^{-1}$), a protein content of 20–30%, a carbohydrate content of 22–32%, and an amino acid composition (molar ratio) of aspartic acid; 9.0%, glutamic acid; 16.1%, glycine; 9.1%, alanine; 12.5%, valine; 5.7%, arginine; 5.6%, and ornithine; 7.8% (including an error of ±3%); and containing glucose as an essential constituent carbohydrate.

2. A biologically active substance EEM-SE obtained by extracting *Flammulina velutipes* with water, a lower alcohol having 1–4 carbon atoms, or a mixed solvent of these, and treating the extract using a molecular sieve method, the biologically active substance EEM-SE having a molecular weight of 6,000–60,000, a maximum value of ultraviolet absorption in water of 255–260 nm, a maximum infrared absorption wave number of 3259, 2927, 1578, 1400, and 1043 $cm^{-1}$ (including an error of ±50 $cm^{-1}$), a protein content of 8–18%, a carbohydrate content of 5–10%, and an amino acid composition (molar ratio) of aspartic acid; 9.1%, glutamic acid; 17.7%, glycine; 14.8%, alanine; 21.9%, valine; 11.8%, arginine; 6.8%, and ornithine; 12.6% (including an error of ±3%); and containing glucose as an essential constituent carbohydrate.

3. The process for producing a biologically active substance EEM-S comprising: extracting at least one mushroom selected from *Lentinus edodes, Flammulina velutipes, Hypsizygus marmoreus, Pleurotus ostreatus, Pholiota nameko, Grifola fondosa, Volvariella speciosa* ver. *speciosa, Lyophllum decastes*, Blanc du pays, *Tricholoma matsutake, Ganoderma lucidum*, and *Phellinus yucatensis* (*Phellinus linteus*), with water, a hydrophilic solvent, or a mixed solvent of these, and treating the extract using a molecular sieve method to collect a fraction having a molecular weight of 6,000–60,000 and a maximum, value of ultraviolet absorption in water of 255–260 nm, wherein the molecular sieve method uses a molecular sieve membrane (flat membrane), a hollow filter membrane, a permeable membrane, or molecular chromatography.

4. The process for producing a biologically active substance EEM-S according to claim 3, wherein the hydrophilic solvent is a lower alcohol having 1–4 carbon atoms.

5. A drug comprising the biologically active substance according to claim 1 as an active ingredient.

6. A drug comprising the biologically active substance according to claim 2 as an active ingredient.

7. A drug comprising the biologically active substance according to claim 3 as an active ingredient.

8. The drug according to claim 5, which is an anticancer agent.

9. The drug according to claim 6, which is an anticancer agent.

10. The drug according to claim 9, which is an anticancer agent.

11. The drug according to claim 5, which is in the form of a tablet, powder, granule, capsule, or liquid.

12. The drug according to claim 6, which is in the form of a tablet, powder, granule, capsule, or liquid.

13. The drug according to claim 9, which is in the form of a tablet, powder, granule, capsule, or liquid.

14. The drug according to claim 5, which is a tablet coated with a soybean peptide and/or shell resin film coat material.

15. The drug according to claim 6, which is a tablet coated with a soybean peptide and/or shell resin film coat material.

16. The drug according to claim 9, which is a tablet coated with a soybean peptide and/or shell resin film coat material.

17. A drug comprising the biologically active substance according to claim 4 as an active ingredient.

18. The drug according to claim 17, which is an anticancer agent.

19. The drug according to claim 17, which is in the form of a tablet, powder, granule, capsule, or liquid.

20. The drug according to claim 17, which is a tablet coated with a soybean peptide and/or shell resin film coat material.

* * * * *

UNITED STATES PATENT AND TRADEMARK OFFICE
CERTIFICATE OF CORRECTION

| | | |
|---|---|---|
| PATENT NO. | : 6,783,771 B2 | Page 1 of 1 |
| APPLICATION NO. | : 10/169099 | |
| DATED | : August 31, 2004 | |
| INVENTOR(S) | : Ikekawa et al. | |

It is certified that error appears in the above-identified patent and that said Letters Patent is hereby corrected as shown below:

On the title page, Item (87), the PCT information in incorrect. Item (87) should read:

-- (87)    PCT Pub. No.: WO01/51070
              PCT Pub. Date: Jul. 19, 2001 --

Signed and Sealed this

Sixth Day of March, 2007

JON W. DUDAS
*Director of the United States Patent and Trademark Office*